(12) United States Patent
Ota

(10) Patent No.: US 8,454,163 B2
(45) Date of Patent: Jun. 4, 2013

(54) OPHTHALMIC IMAGING APPARATUS AND IMAGING METHOD USING OPHTHALMIC IMAGING APPARATUS

(75) Inventor: Yuji Ota, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 7 days.

(21) Appl. No.: 13/208,778

(22) Filed: Aug. 12, 2011

(65) Prior Publication Data

US 2012/0050674 A1 Mar. 1, 2012

(30) Foreign Application Priority Data

Aug. 31, 2010 (JP) .................................. 2010-195067

(51) Int. Cl.
*A61B 3/14* (2006.01)
*A61B 3/02* (2006.01)
*A61B 3/00* (2006.01)

(52) U.S. Cl.
USPC ............................ 351/206; 351/237; 351/246

(58) Field of Classification Search
USPC .................................................. 351/200–246
See application file for complete search history.

(56) References Cited

U.S. PATENT DOCUMENTS

| 5,615,278 A | 3/1997 | Matsumoto | |
|---|---|---|---|
| 2012/0140181 A1* | 6/2012 | Koiwa et al. | 351/237 |
| 2012/0154748 A1* | 6/2012 | Inoue et al. | 351/206 |

FOREIGN PATENT DOCUMENTS

| JP | 03-081879 A | 4/1991 |
|---|---|---|
| JP | 07-255680 A | 10/1995 |
| JP | 2005-261533 A | 9/2005 |

* cited by examiner

*Primary Examiner* — Mohammed Hasan
(74) *Attorney, Agent, or Firm* — Fitzpatrick, Cella, Harper & Scinto (57) ABSTRACT

An ophthalmic imaging apparatus includes an illumination unit configured to illuminate a fundus of an eye to be examined; an imaging unit configured to obtain a fundus image by capturing the illuminated fundus; a detection unit configured to detect flare in an edge portion of the fundus image based on a photometric value of light from the fundus; a control unit configured to control correction processing for the fundus image for adjustment of a light amount at the edge portion of the fundus image in accordance with a flare detection result obtained by the detection unit; and a correction unit configured to perform the correction processing for the fundus image in accordance with the control.

20 Claims, 4 Drawing Sheets

OPHTHALMIC IMAGING APPARATUS AND IMAGING METHOD USING OPHTHALMIC IMAGING APPARATUS

BACKGROUND OF THE INVENTION

1. Field of the Invention

The present invention relates to an ophthalmic imaging apparatus and an imaging method using the ophthalmic imaging apparatus.

2. Description of the Related Art

A fundus image captured by a fundus imaging apparatus using a digital camera may exhibit a lack of light amount due to the influences of vignetting and the like of a photographing optical system. For example, U.S. Pat. No. 5,615,278 discloses an image processing technique for correcting the light falloff of a fundus image to solve this problem.

If, however, light amount correction is performed for a fundus image in which flare is depicted, the flare is emphasized, resulting in an increase in uninterpretable portion.

SUMMARY OF THE INVENTION

The present invention provides an ophthalmic imaging technique which can capture a fundus image without emphasizing flare by switching correction processes based on a flare detection result on the fundus image, depending on whether to process a region including flare or a region including no flare.

According to one aspect of the present invention, there is provided an ophthalmic imaging apparatus comprising: an illumination unit configured to illuminate a fundus of an eye to be examined; an imaging unit configured to obtain a fundus image by capturing the illuminated fundus; a detection unit configured to detect flare in an edge portion of the fundus image based on a photometric value of light from the fundus; a control unit configured to control correction processing for the fundus image for adjustment of pixel values at the edge portion of the fundus image in accordance with a flare detection result obtained by the detection unit; and a correction unit configured to perform the correction processing for the fundus image in accordance with the control.

According to another aspect of the present invention, there is provided an imaging method using an ophthalmic imaging apparatus including an illumination unit configured to illuminate a fundus of an eye to be examined, an imaging unit configured to obtain a fundus image by capturing the illuminated fundus, and a detection unit configured to detect flare in an edge portion of the fundus image based on a photometric value of light from the fundus, the method comprising: a control step of controlling correction processing for the fundus image to adjust pixel values in an edge portion of the fundus image in accordance with a flare detection result obtained by the detection unit; and a correction step of performing the correction processing for the fundus image in accordance with the control.

According to the present invention, it is possible to capture a good fundus image without emphasizing flare by switching correction processes, based on a flare detection result on a fundus image, depending on whether to process a region including flare or a region including no flare.

Further features of the present invention will become apparent from the following description of exemplary embodiments (with reference to the attached drawings).

DESCRIPTION OF THE EMBODIMENTS

First Embodiment

Figure 1:
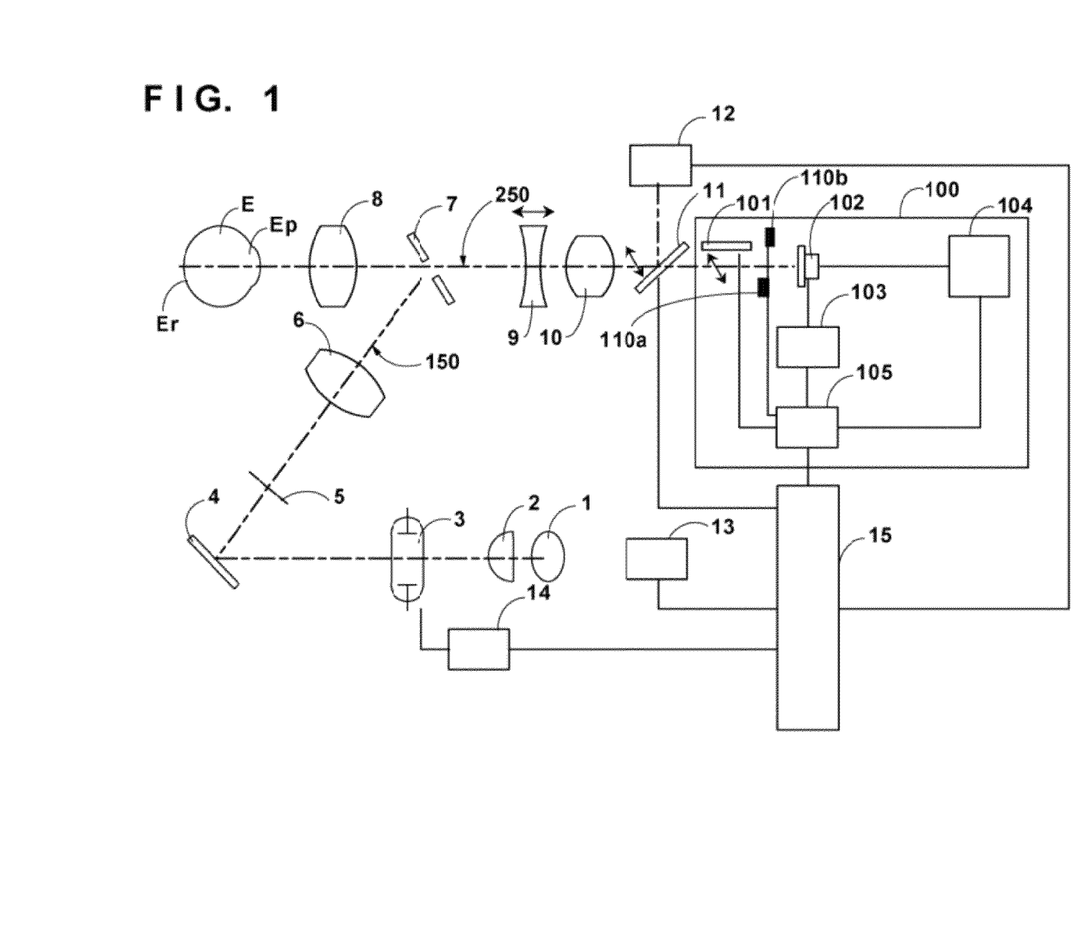
FIG. 1 is a view showing the arrangement of a non-mydriatic type fundus camera according to the first embodiment.

The arrangement of an ophthalmic imaging apparatus (fundus camera) according to the first embodiment of the present invention will be described with reference to FIG. 1. As the ophthalmic imaging apparatus (fundus camera) according to the first embodiment, the arrangement of a non-mydriatic type fundus camera is exemplified. A condenser lens 2, an imaging light source 3, a mirror 4, a stop 5 having a ring-like opening, a relay lens 6, and a perforated mirror 7 are sequentially arranged on the optical path from an observation light source 1 to an objective lens 8. These constituent elements constitute a fundus illumination optical system 150 which guides light to an eye E to be examined. A focus lens 9, a photographing lens 10, and a flip-up mirror 11 are arrayed on an optical path in the transmission direction of the perforated mirror 7. These constituent elements constitute a fundus photographing optical system 250 which guides light to an image sensor 102 mounted in an imaging camera 100. An internal vision fixation lamp 12 on which light-emitting members such as LEDs for inducing the vision fixation of the eye E are aligned and arranged is placed in the reflecting direction of the flip-up mirror 11.

In this case, the observation light source 1 is an LED light source which emits infrared light, and the flip-up mirror 11 is a mirror which transmits infrared light and reflects visible light. On the other hand, although not shown, an LED light source for an alignment index and the exit end of a light guide which guides a light beam from the LED light source are arranged in front of the perforated mirror 7 so as to constitute an alignment index projection system which projects an alignment index on the cornea surface of the eye E. Likewise, although not shown, in the fundus illumination optical system 150, a focus index projection system which projects a focus index on a fundus Er of the eye E is formed. Although the alignment index projection system and the focus index projection system are important components of the ophthalmic imaging apparatus (fundus camera), since they are not required to explain the features of the present invention, detailed description will be omitted.

In addition to the optical arrangement described above, an imaging light source control unit 14, which controls the imaging light source 3, is connected to a system control unit 15 which controls the overall ophthalmic imaging apparatus (fundus camera). An input unit 13 forming an imaging start switch which captures still image of the eye E is connected to the system control unit 15. The system control unit 15 can start capturing still image of the eye E upon receiving an input from the input unit 13.

(Imaging Camera 100)

The schematic arrangement of the imaging camera 100 will be described next. This embodiment can use, for example, a single-lens reflex type digital camera as the imaging camera 100, which is part of the arrangement of the ophthalmic imaging apparatus (fundus camera) described above. The imaging camera 100 is configured to be detachable with the ophthalmic imaging apparatus (fundus camera). Although the imaging camera 100 is constituted by various functional portions, FIG. 1 shows only portions necessary to explain the features of the present invention. The imaging camera 100 includes an imaging camera control unit 105 which controls the overall imaging camera 100, an image sensor 102, a photometric value calculation unit 103 which calculates a photometric value corresponding to an output from the image sensor 102, and a moving image observation monitor 104 such as an LCD.

A flip-up mirror 101 inside the imaging camera 100 and front and rear curtains 110a and 110b as shutter curtains are arranged on the front surface side of the image sensor 102. The imaging camera control unit 105 is connected to the flip-up mirror 101, the front curtain 110a, the rear curtain 110b, the photometric value calculation unit 103, and the moving image observation monitor 104, and controls the overall imaging camera 100. The imaging camera control unit 105 is also connected to the system control unit 15 through an electrical contact.

The operation of each unit will be described next, together with manipulation by the examiner. Operations at the time of alignment will be described first. An infrared light beam emitted from the observation light source 1 passes through the condenser lens 2 and the imaging light source 3 and is reflected by the mirror 4. The light reflected by the mirror 4 passes through the stop 5 having a ring-like opening and the relay lens 6 and is reflected by a periphery of the perforated mirror 7. The reflected light passes through the objective lens 8 and a pupil Ep of the eye E and illuminates the fundus Er. The infrared light reflected by the fundus Er illuminated with the infrared light passes through the pupil Ep of the eye E, the objective lens 8, and the hole of the perforated mirror 7 and is transmitted through the focus lens 9, the photographing lens 10, and the flip-up mirror 11 which reflects visible light and transmits infrared light. The infrared light reflected by the fundus Er is formed into an image on the image sensor 102. After the infrared light emitted from the observation light source 1 is reflected by the fundus Er in this manner, the light is formed into an image on the image sensor 102. The light can be observed as a moving image indicating a live view state on the moving image observation monitor 104.

Figure 2:
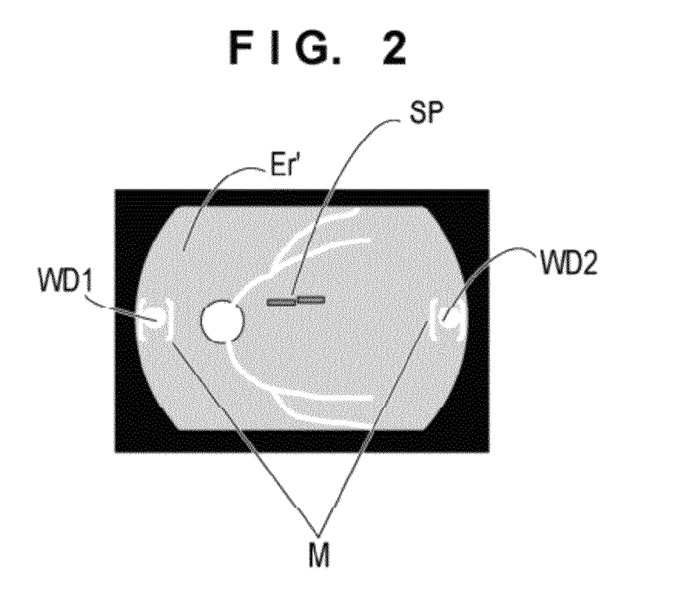
FIG. 2 is a view showing an observation state with the non-mydriatic type fundus camera.

On the other hand, light beams exiting from the alignment index projection system and the focus index projection system are respectively reflected by the cornea surface and fundus Er of the eye to be formed into images on the image sensor 102. It is possible to observe alignment indices WD1 and WD2 and focus indices SP, together with an observation image Er' of the fundus Er, on the moving image observation monitor 104, as shown in FIG. 2. The examiner performs positioning of the eye E and the ophthalmic imaging apparatus (fundus camera) and focus adjustment of the fundus Er so as to set the alignment indices WD1 and WD2 at alignment positions M and align the focus indices SP horizontal.

In this embodiment, at the time of the observation of the fundus, the flip-up mirror 101 which has entered the optical path of the fundus photographing optical system 250 is controlled to a state in which it is retracted from the optical path, and the front and rear curtains 110a and 110b are controlled to an open state. In this state, it is possible to guide reflected light from the fundus Er including the alignment and focus indices onto the image sensor 102.

The photometric value calculation unit 103 has a function of calculating and recording photometric values concerning a plurality of different regions in a fundus image based on the fundus image captured by the image sensor 102. The photometric value calculation unit 103 can calculate photometric values from the observation image captured by the image sensor 102. This photometric value calculation processing by the photometric value calculation unit 103 quantifies information indicating the brightness of an observation image (for example, luminance or brightness information). More specifically, as the fundus reflectance decreases, the photometric value (luminance or brightness) decreases, and vice versa.

The imaging camera control unit 105 has a flare detection function for detecting the presence/absence of flare by comparing photometric values corresponding to a plurality of regions which are recorded by the photometric value calculation unit 103. The imaging camera control unit 105 can switch correction processes for correcting the light amount of a fundus image, based on the flare detection result obtained by the photometric value calculation unit 103, depending on whether to process an image region having flare or an image region having no flare. The contents of specific correction processes will be described later.

The arrangement of the ophthalmic imaging apparatus (fundus camera) according to this embodiment allows for concurrent alignment and photometry of an observation image. That is, this arrangement allows for the calculation of the photometric value of an observation image by using the photometric value calculation unit 103 while performing alignment of the eye E by using the moving image observation monitor 104 of the imaging camera 100.

While the live view function is not used, the imaging camera control unit 105 controls the flip-up mirror 101 to a state in which it is inserted on the optical path of the fundus photographing optical system 250, and controls the front curtain 110a to a closed state. This inhibits reflected light from the fundus Er and the alignment and focus indices from being guided onto the image sensor 102. In this case, since no observation image is captured on the image sensor 102, the photometric value calculation unit 103 calculates no photometric value.

(Flare Detection and Light Amount Correction)

As a flare detection technique, there is available a technique of detecting flare generated in an edge portion of a fundus image by illumination light applied to the anterior segment of an eye to be examined and reflected by the anterior segment of the eye due to the misalignment of the photographing optical system. For example, Japanese Patent Laid-Open No. 7-255680 discloses a flare detection technique of detecting flare by comparing the luminance of the overall fundus of an observation image with the luminance of the central portion of the fundus. In addition, Japanese Patent Laid-Open No. 2005-261533 discloses a technique for determining, as a flare portion, a portion of captured image information in which the spatial frequency is lower than a predetermined level and the luminance value is higher than a predetermined level, and eliminating the flare portion from the image information.

The flare detection techniques disclosed in Japanese Patent Laid-Open Nos. 7-255680 and 2005-261533 need the addition of a dedicated optical system for flare detection and require a dedicated arithmetic processing circuit for captured image information. This complicates the optical system of an ophthalmic imaging apparatus (fundus camera) and requires an increase in the cost of the apparatus.

A flare detection method to be described below provides an imaging technique which can capture a fundus image allowing to detect flare more accurately at high speed without emphasizing the flare, without adding any dedicated optical system and dedicated processing circuit for flare detection.

A flare detection method as processing characteristic to this embodiment and switching of correction processes for correcting edge light falloff of a fundus image based on a flare detection result will be described with reference to FIGS. 3 and 4. A captured fundus image sometimes undergoes a lack of light amount at a peripheral portion due to the influences of vignetting and the like of a photographing optical system. The following will exemplify correction processing for correcting a lack of light amount at an edge portion of a fundus image.

The photometric value calculation unit 103 can calculate the photometric values of a plurality of different regions in a captured fundus image based on the fundus image and record the photometric values on an internal memory (not shown). The photometric value calculation unit 103 can also generate an electronic mask covering the internal region of a fundus image of the fundus Er which is captured by the image sensor 102 in an observation state, and combine the electronic mask with the fundus image of the fundus Er. The photometric value calculation unit 103 can calculate a photometric value in the region of the fundus image which is located inside the electronic mask and in the region of the fundus image which is located outside the electronic mask. Although it is possible to place an optical mask between the flip-up mirror 11 and the imaging camera 100, the use of an electronic mask is more preferable from the viewpoint of not adding any new optical system.

Figure 3:
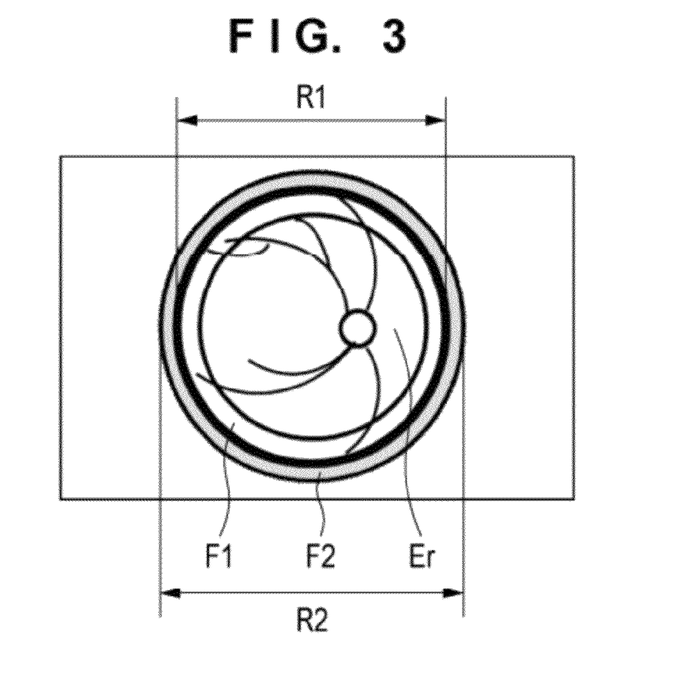
FIG. 3 is a view showing a region of a fundus image used for a flare detection method.
Figure 4:
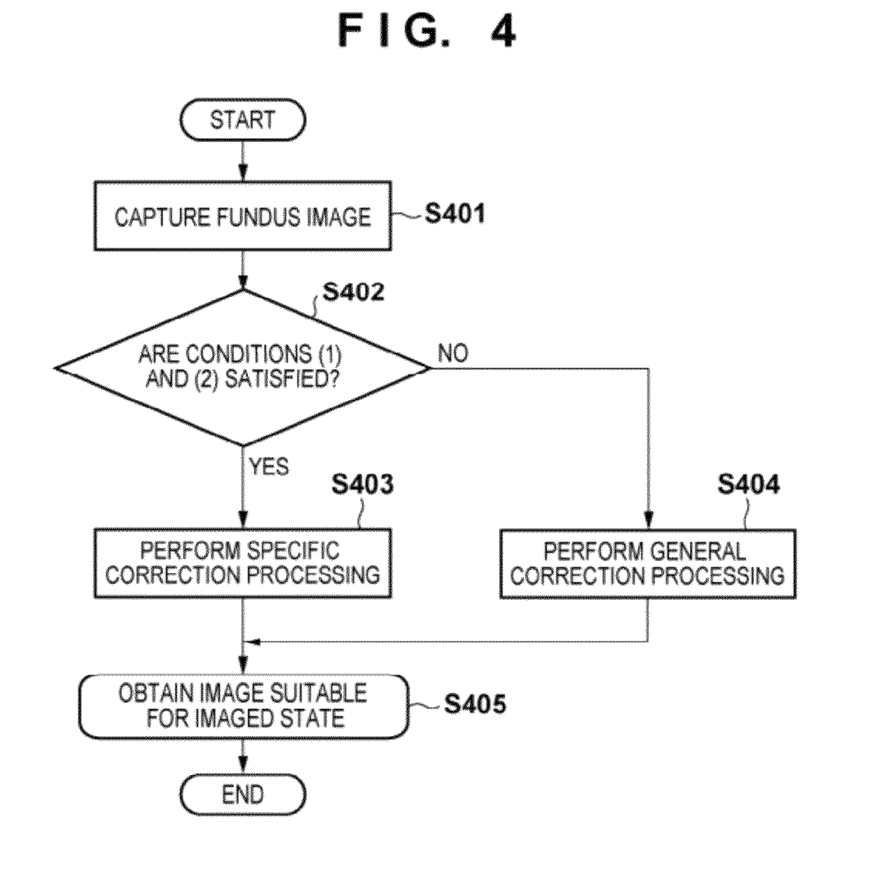
FIG. 4 is a flowchart for explaining a procedure for edge light falloff correction based on a flare detection result.

FIG. 3 shows a fundus image of the fundus Er captured by the image sensor 102 in an observation state. Referring to FIG. 3, reference symbol R1 denotes the size (diameter) of the electronic mask. Letting R2 be the size (diameter) of the fundus image, the relationship between the size of the fundus image and the size of the electronic mask satisfies R2>R1. The internal region of the fundus image of the fundus Er is covered by the electronic mask, and the edge portion of the fundus image is a region (partial display region) which is not covered by the electronic mask. A region F1 indicates the outermost peripheral portion inside the electronic mask, that is, the region of the outermost peripheral portion inside the electronic mask. A region F2 indicates the region of an edge portion of the fundus image which is located outside the electronic mask.

The detection of flare in an edge portion of a fundus image is based on determination results obtained by using photometric values in the regions F1 and F2 at the time of observation under conditions (1) and (2):

Condition (1): The photometric value in the region F2 is larger than the photometric value in the region F1 which are measured (calculated) by the current measurement (Nth measurement: N is a natural number equal to or more than 2 (ditto for the following)).

Condition (2): The photometric value in the region F1 which is measured (calculated) by the current measurement (Nth measurement) is larger than the photometric value average in the electronic mask which is measured (calculated) by the previous measurements (up to the (N−1)th measurement (calculation)).

The imaging camera control unit 105 compares the photometric values in a plurality of regions (for example, the regions F1 and F2) which are obtained by the photometric value calculation unit 103. The imaging camera control unit 105 also calculates the photometric value average of the recorded photometric values in the electronic mask which are measured by the previous measurements up to the (N−1)th measurement, and compares it with the photometric value in the region F1 which is calculated by the current (Nth) measurement. The presence/absence of flare is detected based on the comparison result.

If the photometric value in the region of the fundus image which is located outside the electronic mask is larger than the photometric value in the region of the fundus image which is located inside the electronic mask which is obtained by the Nth measurement, the imaging camera control unit 105 determines that condition (1) is satisfied. If the photometric value, obtained by the Nth measurement, in the region of the fundus image which is located inside the electronic mask is larger than the photometric value average of the recorded photometric values obtained by measurements up to the (N−1)th measurement in the region of the fundus image which is located inside the electronic mask, the imaging camera control unit 105 determines that condition (2) is satisfied. If conditions (1) and (2) simultaneously hold, the imaging camera control unit 105 determines that the image has flare in the region F2 (the region of the fundus image which is located outside the electronic mask). If one of conditions (1) and (2) is not satisfied, the imaging camera control unit 105 determines that the image has no flare in the region F2. Note that when comparing the magnitudes of values in determination based on conditions (1) and (2), it is possible to determine the relationship between the magnitudes of values by determining a threshold for photometric values in advance and determining whether the difference exceeds the threshold.

The imaging camera control unit 105 switches correction processes for correcting the light amount of a fundus image, based on a flare detection result, depending on whether to process a region on the fundus image which has flare or a region on the fundus image which has no flare. A procedure for correction processing (edge light falloff correction processing) will be described with reference to FIG. 4. In this case, edge light falloff correction processing is the processing of correcting the light amount at an edge portion of a fundus image which lacks in light amount due to the influences of vignetting and the like of the photographing optical system. This processing is executed under the overall control of the imaging camera control unit 105.

First of all, in step S401, upon capturing a fundus image, the imaging camera control unit 105 determines the presence/absence of flare in the captured fundus image. In the case shown in FIG. 3, a region in an edge portion of the fundus image is a target of determination of the presence/absence of flare. The determination of the presence/absence of flare is based on conditions (1) and (2) described above. The imaging camera control unit 105 switches correction processes for correcting the light amount of the fundus image, based on the determination result, depending on whether to process a region on the fundus image which has flare or a region on the fundus image which has no flare. When conditions (1) and (2) are simultaneously satisfied (YES in step S402), the imaging camera control unit 105 determines that the target fundus image (the region in the edge portion of the fundus image in the case shown in FIG. 3) has flare. The process then advances to step S403.

In step S403, the imaging camera control unit 105 performs specific correction processing for the region determined to have flare. For example, for the region of the fundus image which has flare, the correction amount for each pixel value in the region obtained by the correction process set by switching can be set to be smaller than that for the region having no flare. It is also possible to switch correction parameters by switching correction parameters for performing correction processing or changing correction function values. Alternatively, it is possible to control the execution of correction processing so as not to perform edge light falloff correction processing. The purpose of this operation is to prevent an increase in uninterpretable portion when flare is emphasized upon applying, to the flare, general edge light falloff correction processing like that applied to a region having no flare.

If the imaging camera control unit 105 determines in step S402 that conditions (1) and (2) are not simultaneously satisfied (NO in step S402), the imaging camera control unit 105 determines that the target fundus image (the region in the edge portion of the fundus image in the case shown in FIG. 3) has no flare. The process then advances to step S404. This is because the problem of an increase in uninterpretable portion does not occur even when edge light falloff correction processing is performed for the image of a region having no flare because no flare is emphasized.

In step S404, the imaging camera control unit 105 controls the execution of correction processing so as to perform general edge light falloff correction processing for the image of the region having no flare. In step S405, the imaging camera control unit 105 generates a fundus image suitable for the imaged state. That is, the imaging camera control unit 105 executes developing processing for the fundus image in accordance with the correction process set by switching (S403 or S404).

In this embodiment, the photometric value calculation unit 103 performs flare detection before imaging by using the photometric values calculated by the photometric value calculation unit 103. However, it is possible to determine the presence/absence of flare from a captured fundus image. It is then possible to apply conditions (1) and (2) described above to a captured fundus image to determine the presence/absence of flare and to perform edge light falloff correction processing.

Second Embodiment

Figure 5:
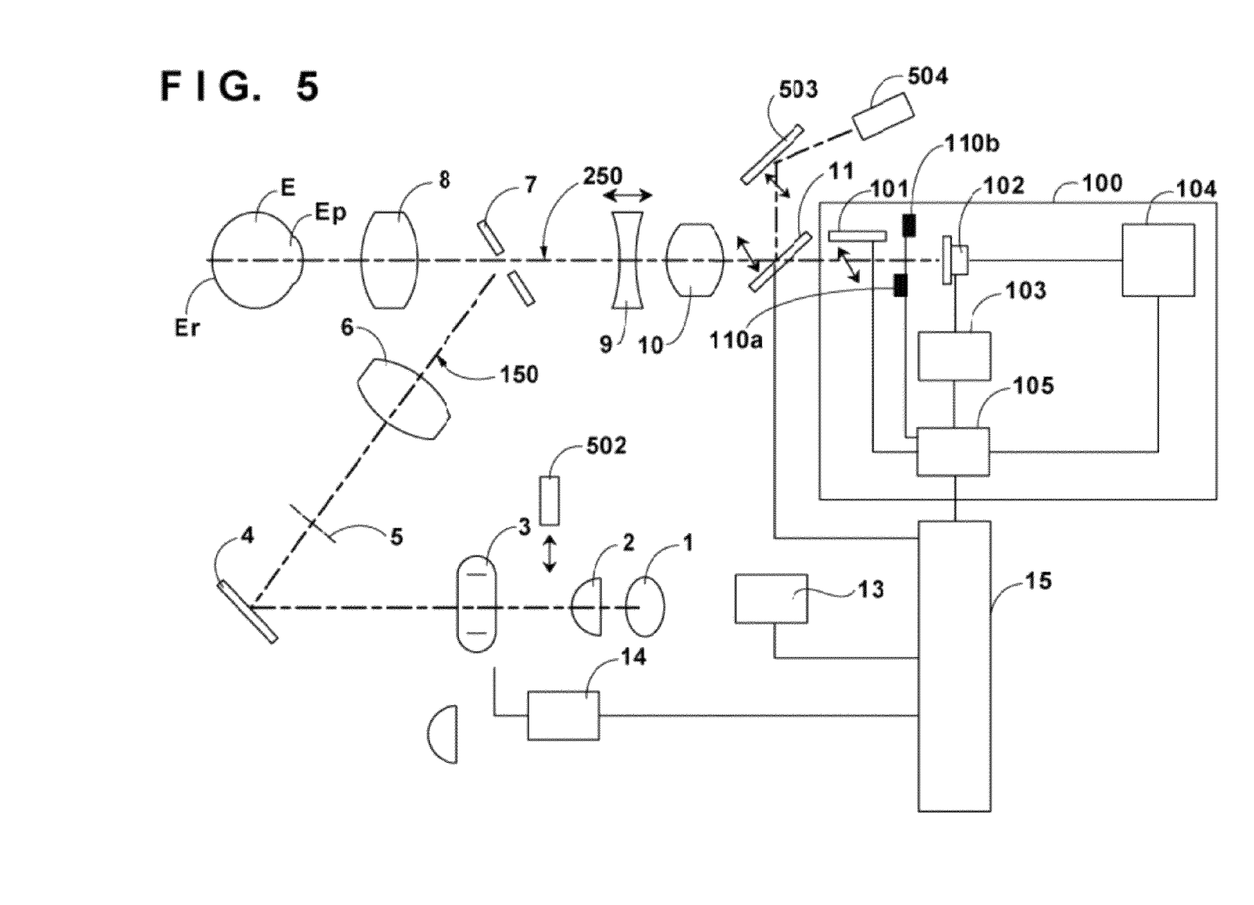
FIG. 5 is a view showing the arrangement of a non-mydriatic type fundus camera according to the second embodiment.

The arrangement of an ophthalmic imaging apparatus (fundus camera) according to the second embodiment of the present invention will be described with reference to FIG. 5. A case in which the ophthalmic imaging apparatus (fundus camera) according to the second embodiment is applied to a non-mydriatic type fundus camera will be described. The same reference numerals as in the arrangement shown in FIG. 1 in the first embodiment denote the same constituent elements in the second embodiment, and a description of them will be omitted. The constituent elements added to the arrangement of the first embodiment (FIG. 1) include an infrared cut filter 502, a detachable reflecting mirror 503, and a direct-view finder 504. The infrared cut filter 502 is detachable with a fundus illumination optical system 150, and is inserted between the condenser lens 2 and the imaging light source 3. The reflecting mirror 503 is placed above the flip-up mirror 11. Light guided from the flip-up mirror 11 is reflected by the reflecting mirror 503, and is guided to the direct-view finder 504 which allows the examiner to observe the eye to be examined with visible light. The second embodiment includes an external vision fixation lamp (not shown) instead of the internal vision fixation lamp in FIG. 1 to allow the examiner to perform fixation-line control more precisely.

An observation light source 1 differs in function from those of the constituent elements of the first embodiment. The first embodiment uses LEDs which emit infrared light. In contrast to this, the second embodiment uses a halogen lamp which emits visible light.

The operation of each unit and manipulation will be described next. At the time of observation using the ophthalmic imaging apparatus (fundus camera) according to the second embodiment, the infrared cut filter 502 is placed at a position retracted from the optical path of the fundus illumination optical system 150. A visible light beam exiting from an observation light source 1 passes through a condenser lens 2 to be applied without losing any infrared components. The subsequent components up to a flip-up mirror 11 are the same as those in the first embodiment, and hence a description of them will be omitted. The flip-up mirror 11 is a mirror which transmits infrared light and reflects visible light, and hence visible light is reflected in the direction of the reflecting mirror 503. The visible light reflected by the reflecting mirror 503 is guided to the direct-view finder 504. The visible light reflected by the reflecting mirror 503 can be observed with the direct-view finder 504. As described above, unlike the first embodiment, the ophthalmic imaging apparatus (fundus camera) according to the second embodiment allows the alignment of an eye E to be examined by direct-vision observation using visible light.

In this case, since an image sensor 102 of an imaging camera 100 directly captures infrared light transmitted through the flip-up mirror 11, it is possible to perform photometry processing like that in the first embodiment. It is possible to apply flare detection processing and the correction processing of correcting edge light falloff of a fundus image based on a flare detection result, which have been described with reference to FIGS. 3 and 4, to the ophthalmic imaging apparatus (fundus camera) according to this embodiment.

The first embodiment allows to perform observation with the moving image observation monitor 104 using the live view function of the imaging camera 100. The second embodiment also allows to perform both infrared observation with the imaging camera 100 and visible light observation with the direct-view finder 504 by performing observation with the moving image observation monitor 104. An imaging camera control unit 105 can save power by performing display control so as to inhibit display on the moving image observation monitor 104.

In addition, a sensor for detecting an examiner who is observing an image from the direct-view finder 504 can be provided near the direct-view finder 504. Furthermore, the imaging camera control unit 105 can control the display operation of the moving image observation monitor 104 so as to inhibit display on the moving image observation monitor 104 by using a detection result from the sensor only when the examiner performs visible light observation.

With the above arrangement, the non-mydriatic type fundus camera which performs visible light observation with the direct-view finder 504 can also obtain the same effects as those of the non-mydriatic type fundus camera which performs infrared observation described in the first embodiment. In addition, since the image sensor 102 in the imaging camera is used both for imaging operation and calculation of photometric values, it is possible to simplify the apparatus as compared with an apparatus including a dedicated sensor for photometry. This embodiment obtains the reflectance of the fundus of an eye to be examined by using the infrared components of light from a halogen lamp configured to emit visible light. In addition, there is conceivable a method of saving the forward/backward moving mechanism of inserting and retracting the infrared cut filter 502 onto and from the optical path by using a mirror configured to transmit visible light for part of the flip-up mirror 11.

According to the first and second embodiments, it is possible to capture a good fundus image without emphasizing flare by switching correction processes, based on a detection result on flare in the fundus image, depending on whether to process a region including flare or a region including no flare.

In addition, using photometric values at the time of observation can detect flare at high speed without adding any new optical system, and using a photometric value in a region outside the electronic mask as well as a photometric value in a region inside the electronic mask can accurately detect flare.

Furthermore, the arrangement configured to detect flare by using a general digital camera can obviate the necessity to provide any dedicated optical system and sensor for flare detection, thereby providing an inexpensive, compact ophthalmic imaging apparatus (fundus camera).

The above embodiments perform the flare detection method by using photometric values for AE, which is periodically repeated, in such a manner that if (1) a photometric value in the region F2 is larger than that in the region F1, and (2) the current photometric value in F1 is larger than the previous photometric value in R1, it is determined that flare is mixed in the image. In general, since a photometric value in R1 at the time of observation of the fundus is small, even if flare is mixed in the image, the photometric value average is smaller than the photometric value in the region F1. Therefore, comparing the photometric value average in R1 at the previous measurement with the photometric value in F1 can specify a state in which flare exists in F1.

In general, when no flare is mixed in a fundus image, the edge portion is darker than the central portion. The above detection method detects relatively strong flare. The reason for the use of the detection method of detecting strong flare but not detecting weak flare is that priority is given to keeping a fundus image as bright as possible by performing correction to brighten an edge portion of the image even if it includes weak flare.

When flare is detected in part of the edge portion of a fundus image, the image provided for a person who performs diagnosis becomes darker without the correction processing of brightening the edge portion, even if the flare included in the portion is weak. Since dark images are not preferable for diagnosis, the light amount at the edge portion is corrected to keep the image bright even if slight flare is detected. For this reason, the embodiments use the above detection method of detecting flare with a predetermined intensity or more.

The above detection method is merely an example, and it is possible to use an arbitrary detection method of detecting flare with a certain intensity. In addition, the imaging camera control unit 105 may perform control to correct the brightness of the edge portion of a fundus image depending on whether flare with an intensity higher than a predetermined intensity is detected by using a method of detecting the intensity of flare. Note, however, that the above detection method facilitates computation processing and can suppress the amount of calculation. It is therefore possible to provide a fundus image which suppresses flare in the image after processing and improves diagnosis accuracy while shortening the delay time from the instant the imaging button is pressed to the instant an image is displayed.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-195067, filed Aug. 31, 2010, which is hereby incorporated by reference herein in its entirety.

What is claimed is:

1. An ophthalmic imaging apparatus comprising:
an illumination unit configured to illuminate a fundus of an eye to be examined;
an imaging unit configured to obtain a fundus image by capturing the illuminated fundus;
a detection unit configured to detect flare in an edge portion of the fundus image based on a photometric value of light from the fundus; and
a control unit configured to control correction processing for the fundus image for adjustment of pixel values at the edge portion of the fundus image in accordance with a flare detection result obtained by said detection unit.

2. The apparatus according to claim 1, wherein said detection unit detects flare in the edge portion of the captured fundus image based on a photometric value of light from the fundus illuminated before capturing of the fundus image.

3. The apparatus according to claim 2, wherein said detection unit obtains the photometric value based on an infrared image of the fundus illuminated before imaging of the fundus.

4. The apparatus according to claim 1, wherein the ophthalmic imaging apparatus is of a non-mydriatic type,
wherein said illumination unit illuminates a fundus with one of visible light and infrared light which does not substantially include visible light, and
wherein flare is detected in the edge portion of the fundus image based on an infrared image of the fundus illuminated with the infrared light.

5. The apparatus according to claim 1, wherein said control unit switches correction processes by switching correction parameters for performing the correction processing or changing a correction function value for performing the correction processing.

6. The apparatus according to claim 1, wherein the photometric value is information indicating brightness of the fundus image captured by said imaging unit.

7. The apparatus according to claim 1, further comprising a correction unit configured to perform the correction processing for the fundus image in accordance with the control.

8. The apparatus according to claim 7, further comprising a calculation unit configured to calculate photometric values in a plurality of different regions of the fundus image captured by said imaging unit by measuring the respective regions,
wherein said detection unit detects the presence/absence of flare in the region in which the photometric value is measured, by comparing the photometric values calculated by said calculation unit,
wherein said control unit switches correction processes for correcting a lack in light amount in the fundus image, based on a detection result obtained by said detection unit, depending on whether to process a region on the fundus image which has the flare or a region on the fundus image which does not have the flare, and
wherein said correction unit performs developing processing for the fundus image in accordance with the correction process set by switching by said control unit.

9. The apparatus according to claim 8, wherein a correction amount obtained by the correction process set by switching the region on the fundus image which has the flare is smaller than a correction amount for the region on the fundus image which does not have the flare.

10. The apparatus according to claim 8, wherein said calculation unit generates an electronic mask covering an internal region of the fundus image and calculates the photometric values in a region of the fundus image which is located inside the electronic mask and a region of the fundus image which is located outside the electronic mask, and wherein said detection unit determines that a region outside the electronic mask is a region having the flare, if a photometric value in a region of the fundus image which is located outside the electronic mask is larger than a photometric value in a region of the fundus image which is located inside the electronic mask in Nth (N: a natural number not less than 2) measurement by said calculation unit, and the photometric value in the region inside the electronic mask at the Nth measurement is larger than a photometric value average in the region inside the electronic mask in measurements up to (N−1)th measurement.

11. The apparatus according to claim 7, wherein said control unit controls execution of correction processing so as to perform light falloff correction processing for the fundus image of the region having no flare, and wherein said control unit controls execution of correction processing so as not to perform light falloff correction processing for the fundus image of the region having flare.

12. The apparatus according to claim 1, further comprising an illumination optical unit which guides light to an eye to be examined via a ring-like opening portion arranged on an optical path.

13. The apparatus according to claim 1, wherein said calculation unit calculates photometric values while performing alignment of an eye to be examined.

14. The apparatus according to claim 13, said calculation unit does not calculate the photometric values in a case where a live view function is not used.

15. The apparatus according to claim 13, further comprising an optical mask which is arranged on an optical path and covers an internal region of the fundus image, wherein said calculation unit calculates a photometric value in a region of the fundus image which is located inside the optical mask and calculates a photometric value in a region of the fundus image which is located outside the optical mask.

16. The apparatus according to claim 1, further comprising an observer detection unit configured to detect an observer who is observing an image from a finder, wherein said control unit controls a display on a monitor by using a detection result of said observer detection unit.

17. An imaging method using an ophthalmic imaging apparatus including an illumination unit configured to illuminate a fundus of an eye to be examined, an imaging unit configured to obtain a fundus image by capturing the illuminated fundus, and a detection unit configured to detect flare in an edge portion of the fundus image based on a photometric value of light from the fundus, the method comprising:

a control step of controlling correction processing for the fundus image to adjust pixel values in an edge portion of the fundus image in accordance with a flare detection result obtained by the detection unit.

18. The method according to claim 17, further comprising a correction step of performing the correction processing for the fundus image in accordance with the controlling.

19. An ophthalmic imaging apparatus comprising:
an illumination unit configured to illuminate a fundus of an eye to be examined;
an imaging unit configured to obtain a fundus image by capturing the illuminated fundus;
a detection unit configured to detect flare in an edge portion of the fundus image based on a photometric value of light from the fundus; and
a control unit configured to switch correction processes for correcting a lack in light amount in the fundus images, based on the detection result obtained by said detection unit, depending on whether to process a region on the fundus image which has flare or a region on the fundus image which has no flare.

20. An imaging method using an ophthalmic imaging apparatus including (a) an illumination unit configured to illuminate a fundus of an eye to be examined, (b) an imaging unit configured to obtain a fundus image by capturing the illuminated fundus, and (c) a detection unit configured to detect flare in an edge portion of the fundus image based on a photometric value of light from the fundus, the method comprising:

a control step of switching correction processes for correcting a lack in light amount in the fundus images, based on the detection result obtained by the detection unit, depending on whether to process a region on the fundus image which has flare or a region on the fundus image which has no flare.

* * * * *